United States Patent
Oepen et al.

(10) Patent No.: US 8,979,916 B2
(45) Date of Patent: *Mar. 17, 2015

(54) APPARATUS FOR DELIVERY AND DEPLOYMENT OF AN EXPANDABLE STENT WITHIN A BLOOD VESSEL

(75) Inventors: Randolf Von Oepen, Los Altos Hills, CA (US); Volker Trosken, Bochum (DE); Volker Marx, Hechingen (DE); Armin Stopper, Haigerloch (DE); Louise Balfe, Tubingen (DE); Lorcan James Coffey, Tubingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 1089 days.

This patent is subject to a terminal disclaimer.

(21) Appl. No.: 13/012,587

(22) Filed: Jan. 24, 2011

(65) Prior Publication Data
US 2011/0160847 A1    Jun. 30, 2011

Related U.S. Application Data

(63) Continuation of application No. 10/523,596, filed as application No. PCT/EP03/08795 on Aug. 7, 2003, now Pat. No. 7,875,067.

(30) Foreign Application Priority Data

Aug. 7, 2002   (EP) .................................... 02017696

(51) Int. Cl.
    *A61F 2/06*      (2013.01)
    *A61F 2/958*    (2013.01)
(52) U.S. Cl.
    CPC .................................... *A61F 2/958* (2013.01)
    USPC .......................................................... 623/1.11
(58) Field of Classification Search
    USPC ........ 623/1.11–1.35; 606/108, 194, 198, 200; 604/99.01, 103.05
    See application file for complete search history.

(56) References Cited

U.S. PATENT DOCUMENTS

| | | | | |
|---|---|---|---|---|
| 3,605,745 | A | * | 9/1971 | Hodosh .......................... 604/143 |
| 4,116,201 | A | * | 9/1978 | Shah ........................ 128/207.15 |
| 5,445,646 | A | * | 8/1995 | Euteneuer et al. ............ 606/198 |

(Continued)

FOREIGN PATENT DOCUMENTS

| EP | 1388328 | 2/2004 |
|---|---|---|
| WO | WO 95/11055 | 4/1995 |

(Continued)

OTHER PUBLICATIONS

U.S. Appl. No. 10/523,596, Oct. 14, 2008, Office Action.

(Continued)

*Primary Examiner* — Katherine Dowe
*Assistant Examiner* — Amy Shipley
(74) *Attorney, Agent, or Firm* — Workman Nydegger; Jonathan D. Feuchtwang

(57) ABSTRACT

An improved apparatus for delivering and deployment of an expandable stent with a protection sheath within a blood vessel is provided. The system comprises a fluid pressure device which is coupled with a retraction device for the protection sheath such that after retraction of the protection sheath the stent is automatically deployed by the fluid pressure device. The advantage of the invention is an easy and simple operation of the apparatus.

18 Claims, 19 Drawing Sheets

(56) References Cited

U.S. PATENT DOCUMENTS

| | | | | |
|---|---|---|---|---|
| 5,571,135 | A * | 11/1996 | Fraser et al. | 623/1.12 |
| 5,817,101 | A * | 10/1998 | Fiedler | 623/1.11 |
| 6,056,759 | A * | 5/2000 | Fiedler | 623/1.11 |
| 6,059,813 | A * | 5/2000 | Vrba et al. | 606/198 |
| 6,113,608 | A * | 9/2000 | Monroe et al. | 623/1.11 |
| 6,168,617 | B1 * | 1/2001 | Blaeser et al. | 623/1.11 |
| 6,514,261 | B1 * | 2/2003 | Randall et al. | 606/108 |
| 6,702,843 | B1 * | 3/2004 | Brown et al. | 623/1.11 |
| 6,736,839 | B2 * | 5/2004 | Cummings | 623/1.11 |
| 7,122,050 | B2 * | 10/2006 | Randall et al. | 623/1.23 |
| 7,163,552 | B2 * | 1/2007 | Diaz | 623/1.12 |
| 7,875,067 | B2 * | 1/2011 | Von Oepen et al. | 623/1.11 |
| 2003/0125764 | A1 * | 7/2003 | Brady et al. | 606/200 |
| 2003/0144671 | A1 * | 7/2003 | Brooks et al. | 606/108 |

FOREIGN PATENT DOCUMENTS

| | | |
|---|---|---|
| WO | WO 00/18330 | 4/2000 |
| WO | WO 2004/014256 | 2/2004 |

OTHER PUBLICATIONS

U.S. Appl. No. 10/523,596, Jan. 28, 2009, Office Action.
U.S. Appl. No. 10/523,596, Jul. 1, 2009, Office Action.
U.S. Appl. No. 10/523,596, Dec. 9, 2009, Office Action.
U.S. Appl. No. 10/523,596, Apr. 19, 2010, Notice of Allowance.
U.S. Appl. No. 10/523,596, Sep. 16, 2010, Notice of Allowance.

* cited by examiner

APPARATUS FOR DELIVERY AND DEPLOYMENT OF AN EXPANDABLE STENT WITHIN A BLOOD VESSEL

CROSS-REFERENCE TO RELATED APPLICATIONS

This application is a continuation of U.S. application Ser. No. 10/523,596, filed Dec. 2, 2005, now U.S. Pat. No. 7,875,067, which is a 371 of International Application No. PCT/EP03/08795 filed Aug. 7, 2003, which claims priority to European Application No. 02017696.2 filed Aug. 7, 2002, which prior applications are hereby incorporated by reference in their entireties.

FIELD OF THE INVENTION

The invention relates to a system for delivering a stent into a blood vessel for use e.g. by a physician in a well-known manner for supporting and/or reinforcing the vessel walls and maintaining the vessel in an open, unobstructed condition. It is well-known in the prior art that the stent can be covered and secured in a catheter by a sheath during tracking and delivery in the blood vessel.

BACKGROUND OF THE INVENTION

Furthermore, it is known that the sheath is retracted before positioning the stent within the vessel. A stent delivery system according to U.S. Pat. No. 6,168,617 comprises a catheter with a balloon for inflating a stent which is covered during delivering by a sheath. The sheath is axially moveable on the shaft of the catheter and can be retracted in proximal direction by pull-back means.

U.S. Pat. No. 5,113,608 discloses a stent delivery device which comprises a hydraulically actuated retractable sheath. A pressurising fluid is either supplied by an inflation volume to a portion of a piston housing or is withdrawn from a portion of a piston housing, thereby actuating a piston. As the piston moves the sheath is retracted.

It is the object of the invention to provide an improved stent delivery system with a protection sheath on the stent wherein its handling is simplified.

The object is achieved by the features of the claims.

In order to achieve the object, the invention is based on the following basic ideas.

BRIEF SUMMARY

A device for retracting the sheath is coupled with a fluid pressure device for the inflation and deflation of expandable means (balloon) for deploying the stent. A pressurised fluid, e.g. a liquid or a gas, is supplied from the fluid pressure device to the refraction device and causes the retraction of the sheath. After or during the refraction of the sheath, the pressurised fluid of the cylinder is directed to the expandable means for expansion and deployment of the stent. According to the invention, the expansion of the stent is controlled by the position of the piston within the cylinder. Thus, an automatic inflation of the expandable means after or during retraction of the sheath can be achieved.

The invention has the following advantages. The protection sheath is withdrawn by activating the fluid pressure device, which also controls the expansion of the stent by means of the expansion means. Furthermore, stent-loss and pop-open by using bi-stable stent designs such as Biflex-stents do not occur. There is also no flaring of stainless steel stents and no significantly increased profiles (sheath thickness 0.01 to 0.02 mm). If a drug coated stent is used, no drug will be lost during handling.

BRIEF DESCRIPTION OF THE DRAWINGS

In the following, the invention will be explained in more detail with respect to the figures.

DETAILED DESCRIPTION

Figure 1:
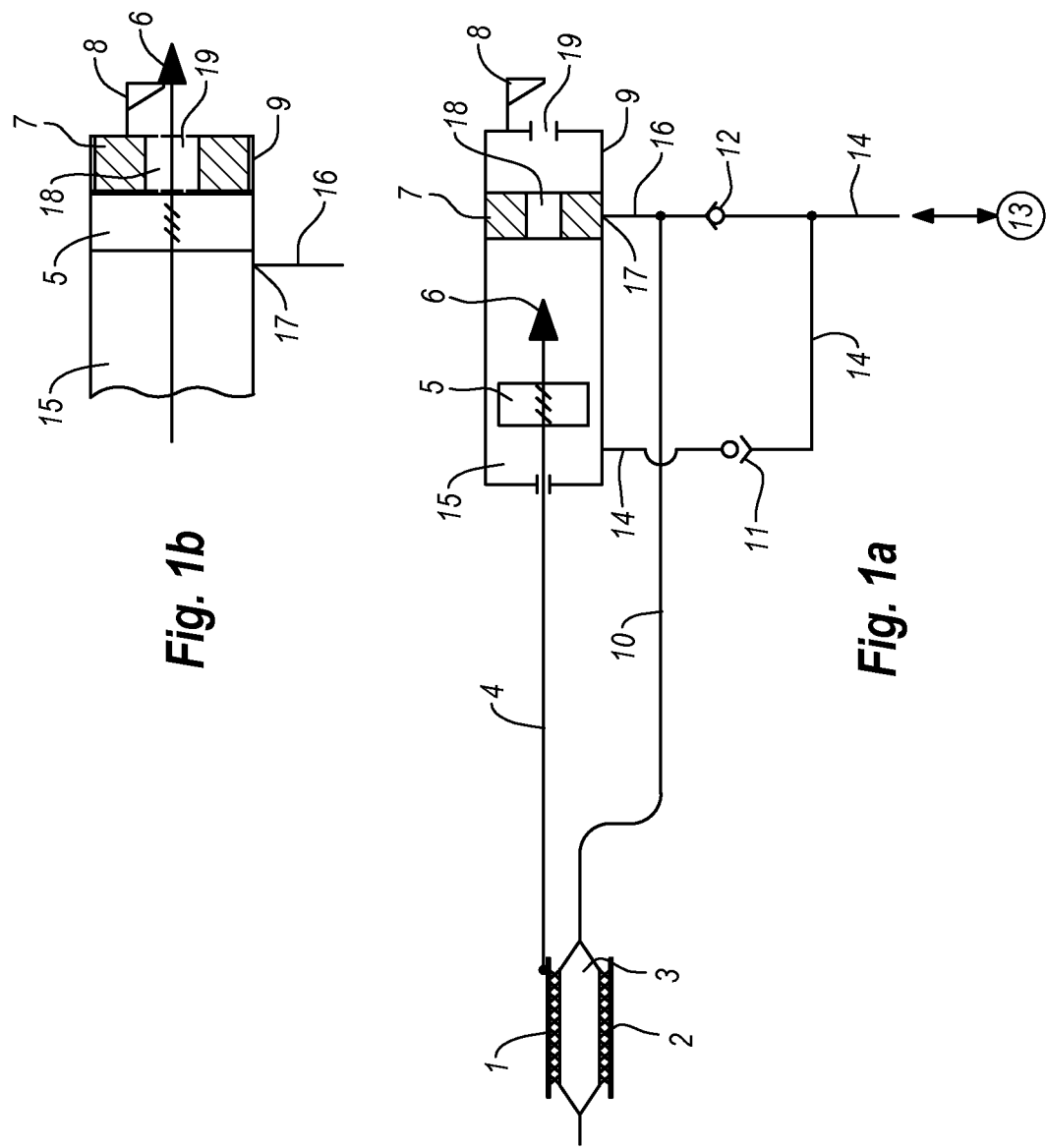
FIG. 1a is a schematic illustration of a first inventive embodiment.
FIG. 1b shows the partial proximal end of the cylinder 15 in FIG. 1a after refraction of the sheath.

In the first inventive embodiment of FIG. 1a, a sheath 1 is arranged on a stent 2 supported by an expandable means 3, preferably an inflatable balloon. The arrangement 1, 2 and 3 is supported by a catheter (not shown) and inserted into a blood vessel. Furthermore, a sheath retraction device 5 to 9, 11 and 13 to 15 and a fluid pressure device 11 to 14 are connected with the arrangement 1 to 3 by a wire 4 and a tube 10, respectively. The wire 4 connects the sheath 1 with a first piston 5 in a cylinder 15 comprising a cylinder housing 9. A hook 6 is connected at the proximal side of the piston 5. The cylinder 15 further comprises a floating second piston 7 with an opening 18 which can be penetrated by the hook 6. The floating piston 7 closes an outlet 17 in the cylinder 15. The tube 10 connects the expandable means 3 with a tube 16 mounted at the outlet 17 of the cylinder 15. A tube 14 is connected to a inflation/deflation device schematically shown as double-arrow 13 at the one end and via a unidirectional valve (check valve) 11 with the cylinder 15 at the other end. Furthermore, the tube 14 is connected via a unidirectional valve (check valve) 12 with the tube 10.

The first inventive embodiment operates as follows. In the arrangement of FIG. 1a the expandable means 3 is in a deflated state and the sheath 1 covers the stent 2. The floating second piston 7 is positioned so that the opening 17 of the cylinder housing 9 and, thus, the tube 16 are closed. An operator (physician) applies pressure from the inflation/deflation device 13 to the tube 14. The pressure shuts the unidirectional valve 12 and opens the unidirectional valve 11. Thus, the pressurised fluid flows into the cylinder 15 and shifts the first piston 5 with the wire 4 and the sheath 1 in proximal direction, i.e. the sheath 1 is retracted from the stent 2. The pressure necessary for moving the piston 5 is very low. When the first piston 5 reaches the floating second piston 7, the proximal end of the wire 4 with the hook 6 penetrates the opening 18 in the piston 7, and the piston 5 moves the piston 7 to the proximal end of the cylinder 15. Thereby, the hook 6 engages the hook holder 8 wherein the piston 5 with the wire 4 and the sheath 1 is fixed at the proximal end. This fixed position of the pistons 5 and 7 is shown in FIG. 1b. In this position, the sheath is completely removed (not shown) from the stent 2, and the outlet 17 of the cylinder 15 is open towards the cylinder chamber. In this manner, the pressurized fluid from the inflation/deflation device 13 flows via the tube 14 and the left side of the cylinder 15 through the outlet 17, the tube 16 and the tube 10 to the expandable means 3, inflates it and deploys the stent 2. The pressure is applied until a required stent diameter is reached. Then, the operator applies a vacuum from the inflation/deflation device 13 via the unidirectional valve 12 and the tube 10 to the expandable means 3. During this suction, the unidirectional valve 11 is closed. At the end of the stent delivery and deployment process, the catheter with the expandable means and the sheath is removed from the blood vessel and the stent remains in the desired position within the blood vessel.

Figure 2:
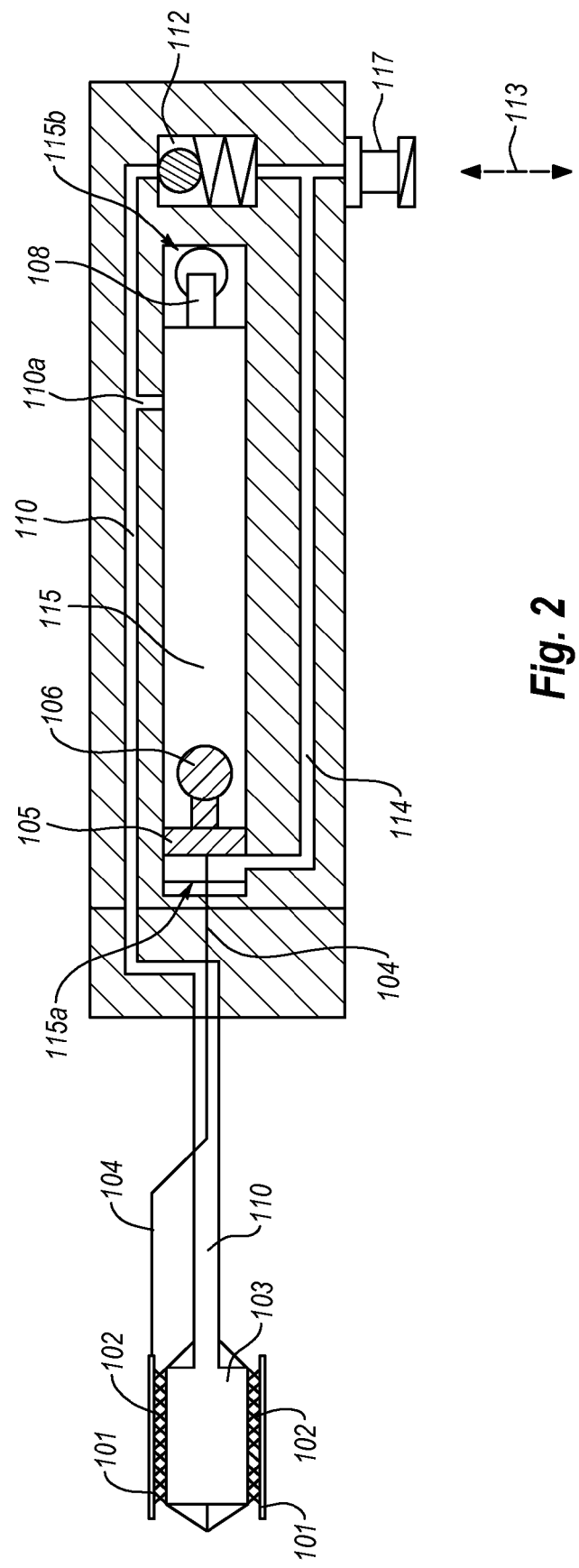
FIG. 2 is a schematic illustration of a second inventive embodiment.
Figure 3:
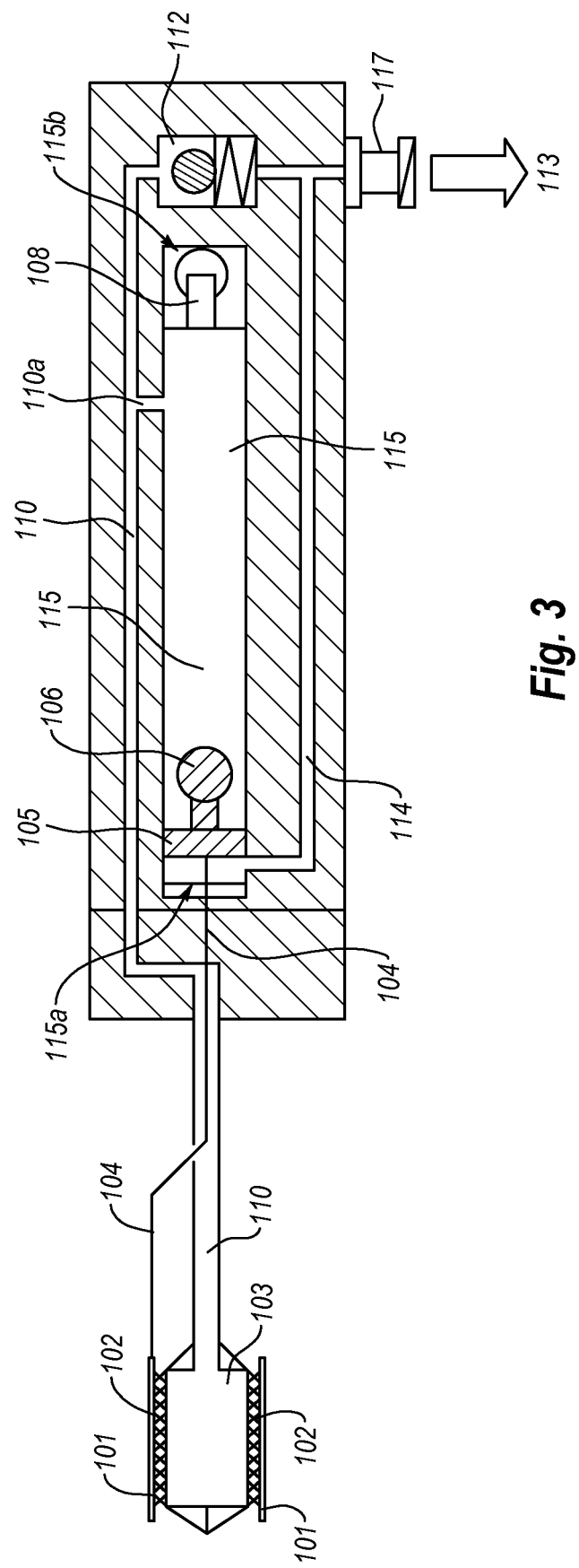
FIGS. 3-10 show steps of the method of operation of the second inventive embodiment.
Figure 4:
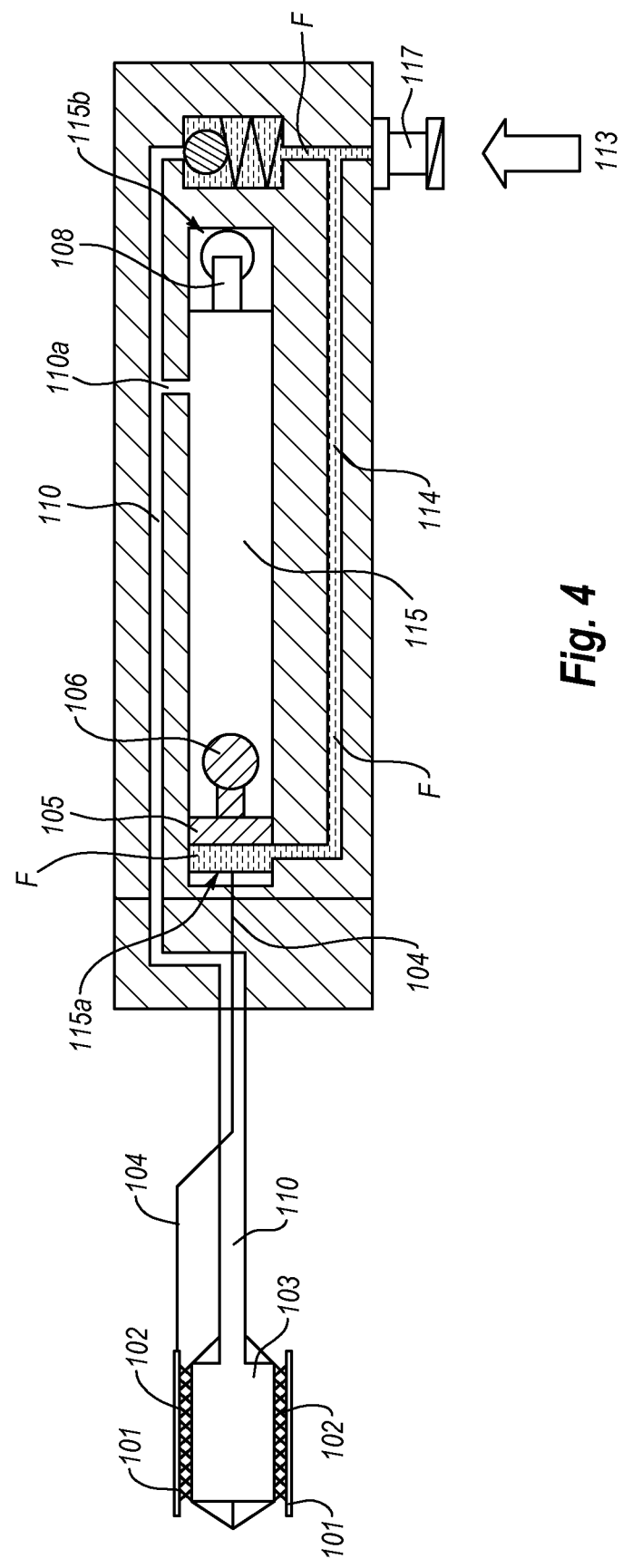
Figure 5:
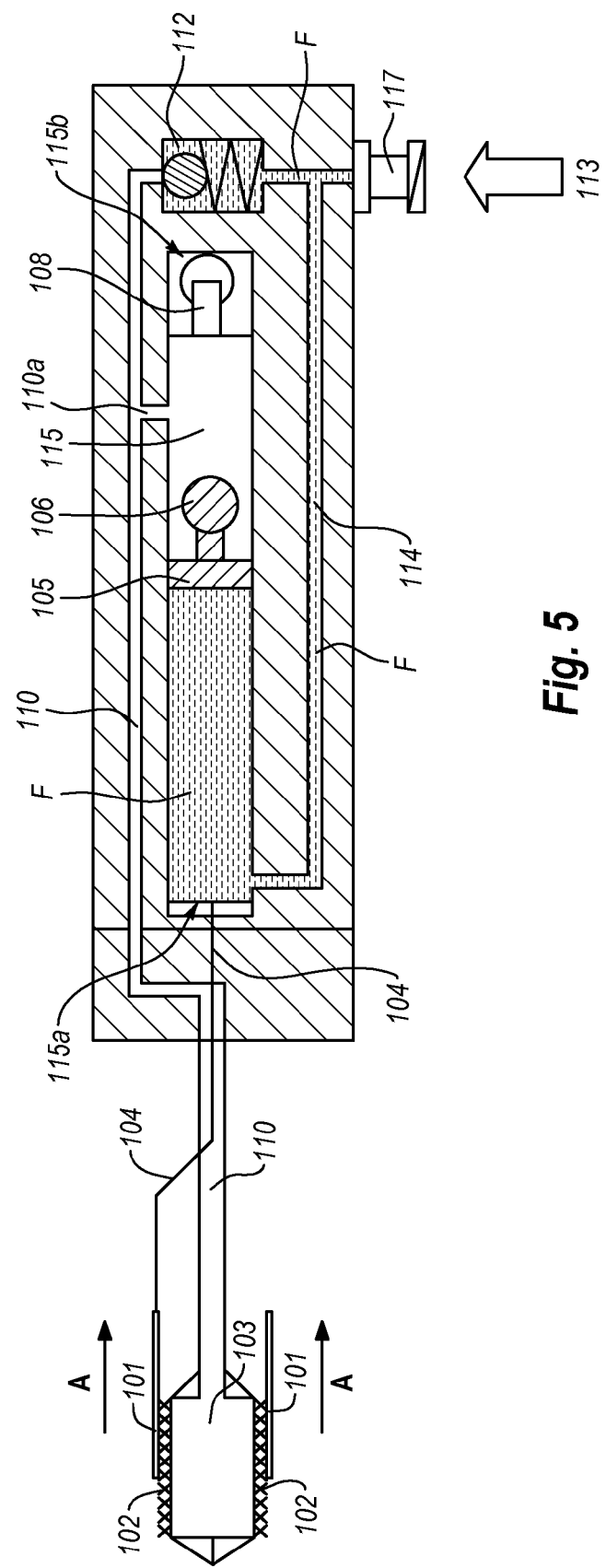

In the second inventive embodiment of FIG. 2 as in FIG. 1a, a protective cover sheath 101 is arranged on a stent 102 supported by an expandable means 103 being an inflatable balloon. As in FIG. 1a, the arrangement 101, 102 and 103 is supported by a catheter (not shown) and is inserted into a blood vessel. The arrangement 101, 102 and 103 is connected via a pull-wire 104 to a cylinder-piston arrangement 105, 106, 108, 110, 110a, 112 and 114. The cylinder-piston arrangement is connected to an inflation/deflation device schematically shown as an arrow 113. A piston 105 with a connector ball 106 is arranged in the cylinder 115 at its distal end 115a. The wire 104 is fixed at the piston. At the proximal end 115b of the cylinder 115a receiving socket 108 is located, into which the connector ball engages when the piston arrives at the end, i.e. the right-hand side in FIG. 2, of the cylinder 115. Furthermore, the cylinder-piston arrangement comprises a unidirectional valve 112, fluid pressure lines 114, 110, 110a and an inlet/outlet 117 as connection to the inflation/deflation device 113.

With respect to FIGS. 3-10, the steps of operation of the second inventive embodiment are shown. In the second and subsequently in the third inventive embodiment, the fluid F is illustrated by black colour.

Figure 6:
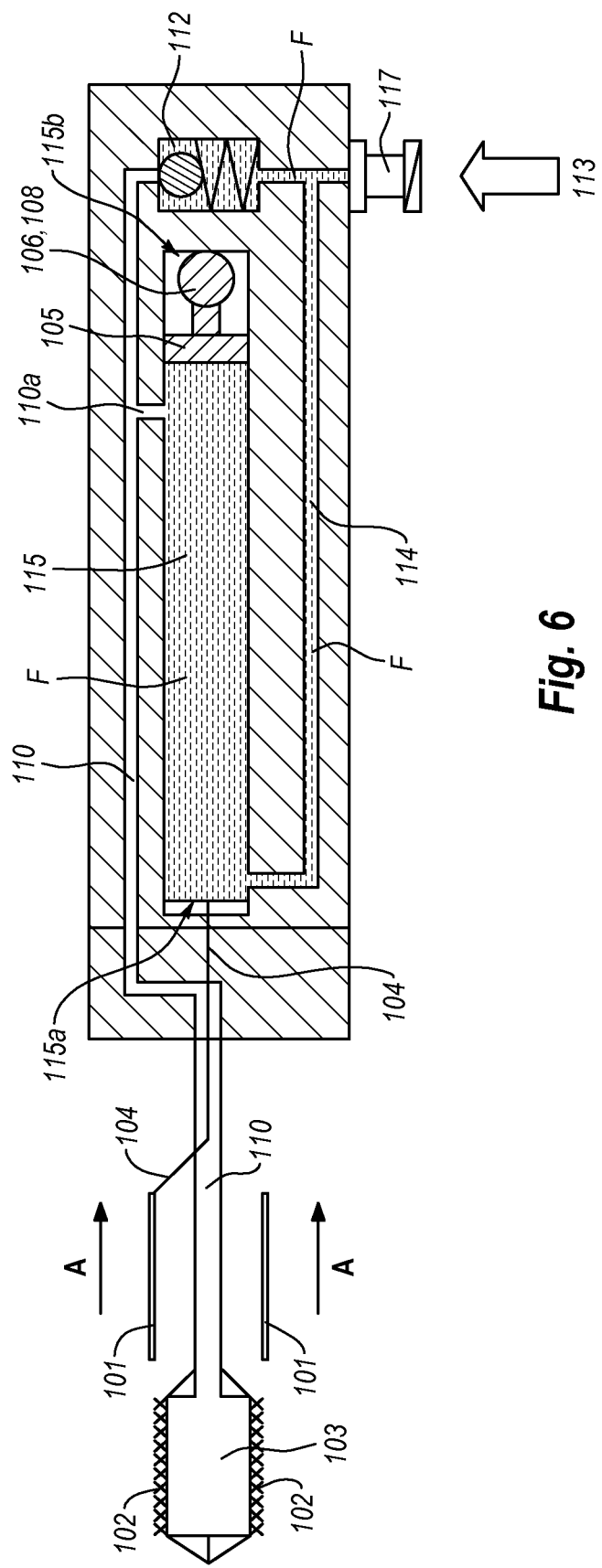
Figure 7:
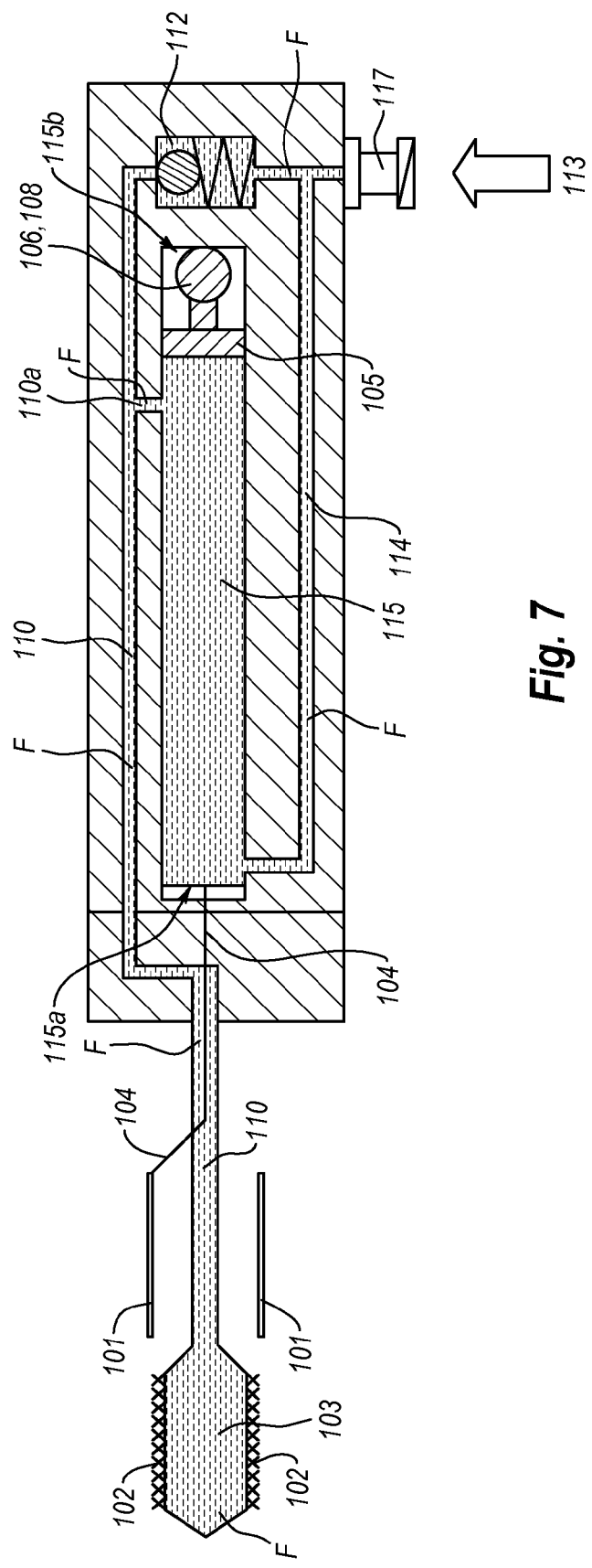
Figure 8:
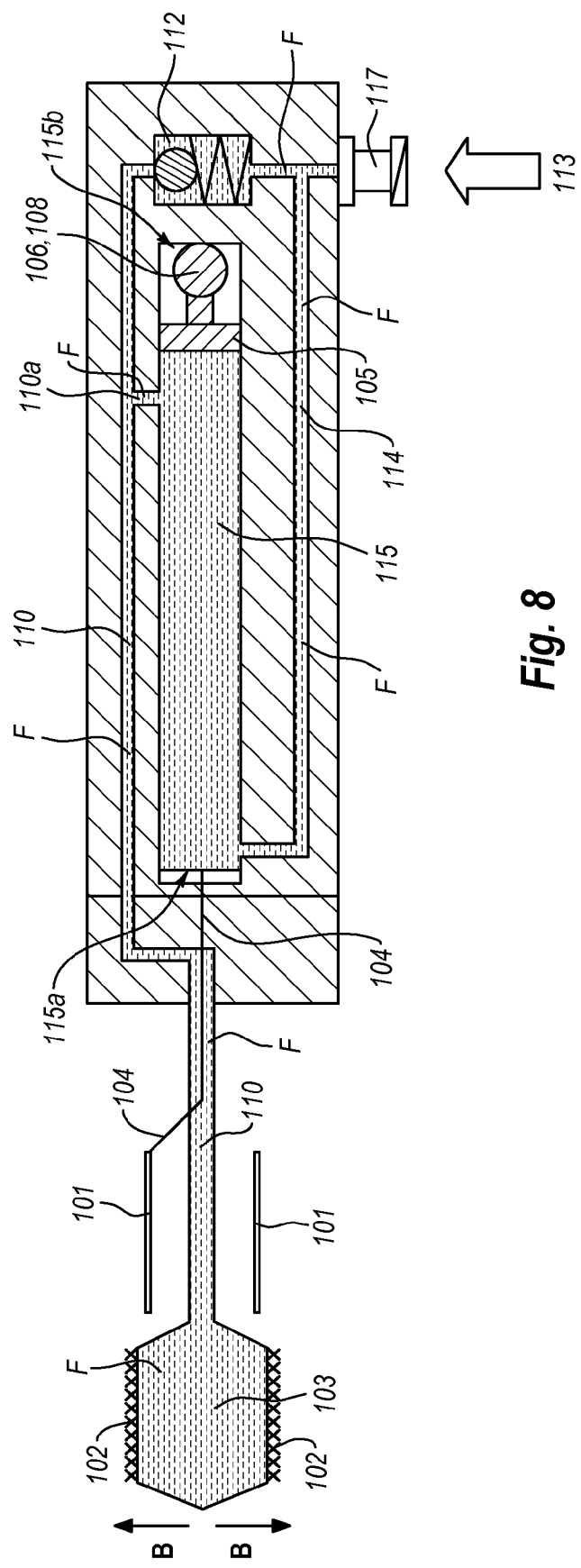
Figure 9:
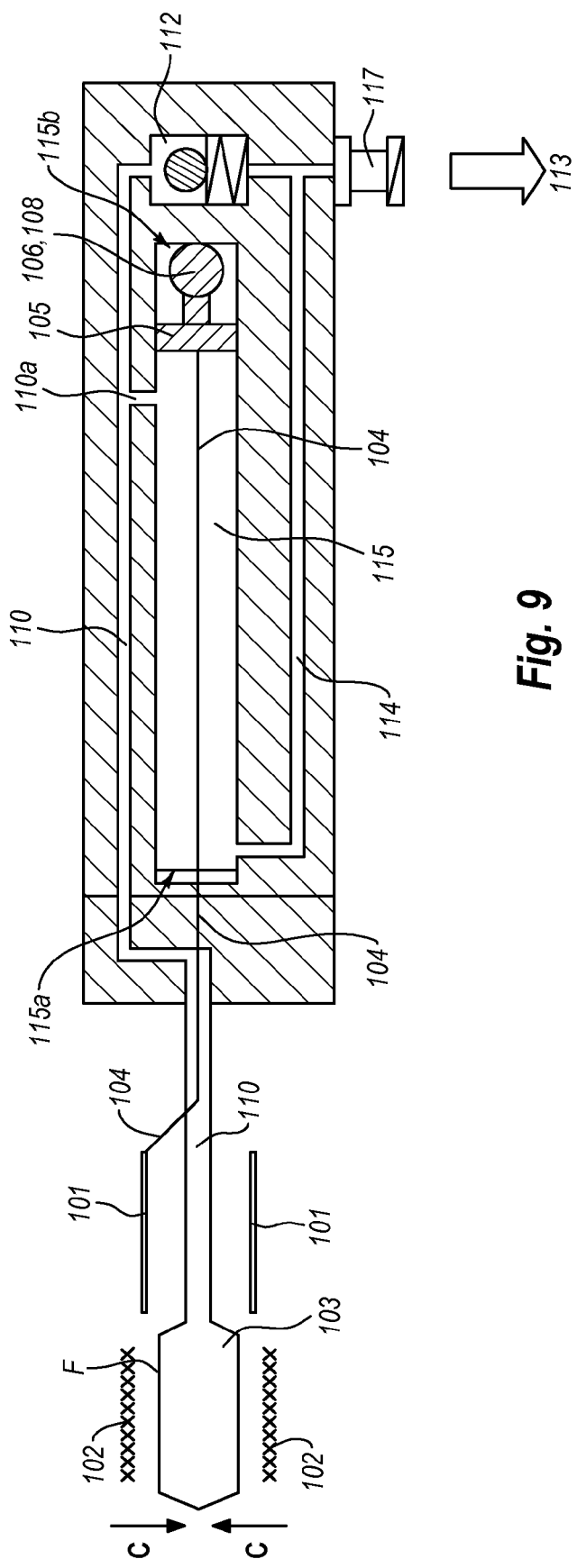
Figure 10:
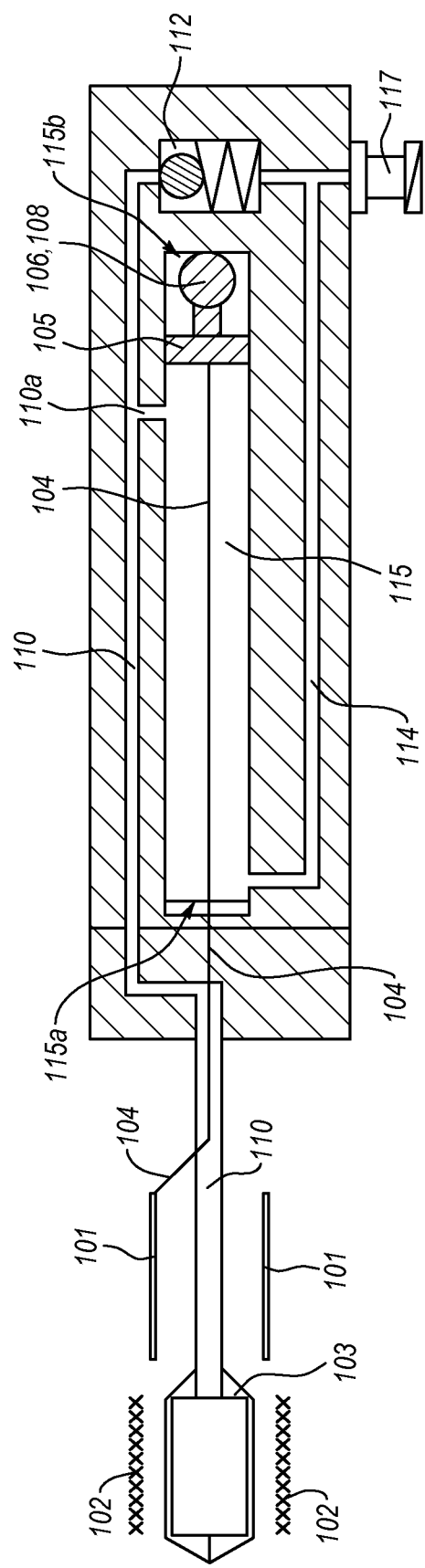

Firstly, vacuum from the inflation/deflation device 113 is applied (FIG. 3) in order to purge air from the catheter and the sheath retraction apparatus. In this state, the unidirectional valve 112 is opened and all parts of the apparatus are in connection with the vacuum. After removing the air from the apparatus, pressurized fluid F (e.g. liquid) is introduced from the inflation/deflation device 113 via the inlet/outlet 117. The pressurized fluid F shuts the unidirectional valve 112 and enters the cylinder 115 at its distal end 115a behind the piston 105 (i.e. at the left-hand side of the piston in FIG. 4). The pressurized fluid F moves the cylinder 105 in proximal direction wherein the wire 104 retracts the protective cover sheath 101 from the stent 102 (arrow A in FIG. 5). During this procedure, the liquid is prevented from entering the catheter and the expandable means 103. As shown in FIG. 6, after arrival of the piston 105 at the proximal end 115b of the cylinder 115, the cover sheath 101 is completely removed from the stent 102, the connector ball 106 is engaged in the receiving socket 108 and a opening 110a, which penetrates the cylinder wall to the fluid pressure line 110 is opened. The pressurized fluid F from the inflation/deflation device 113 via the line 114 and the cylinder 115 enters the line 110 and inflates the expandable means 103 (FIG. 7). The expandable means (balloon) 103 expands and the stent 102 is deployed and contacts the wall of the blood vessel (FIG. 8). Thereafter, the fluid is withdrawn and a vacuum is again applied by means of the inflation/deflation device 113 to deflate the balloon while the piston 105 and the cover sheath 101 remain fixed (FIG. 9). In FIG. 10, the system is fully purged of fluid (e.g. liquid) and the balloon 103 can be re-inflated if necessary, or the expandable means and sheath may be removed from the blood vessel while the stent remains in the desired position within the blood vessel.

Figure 11:
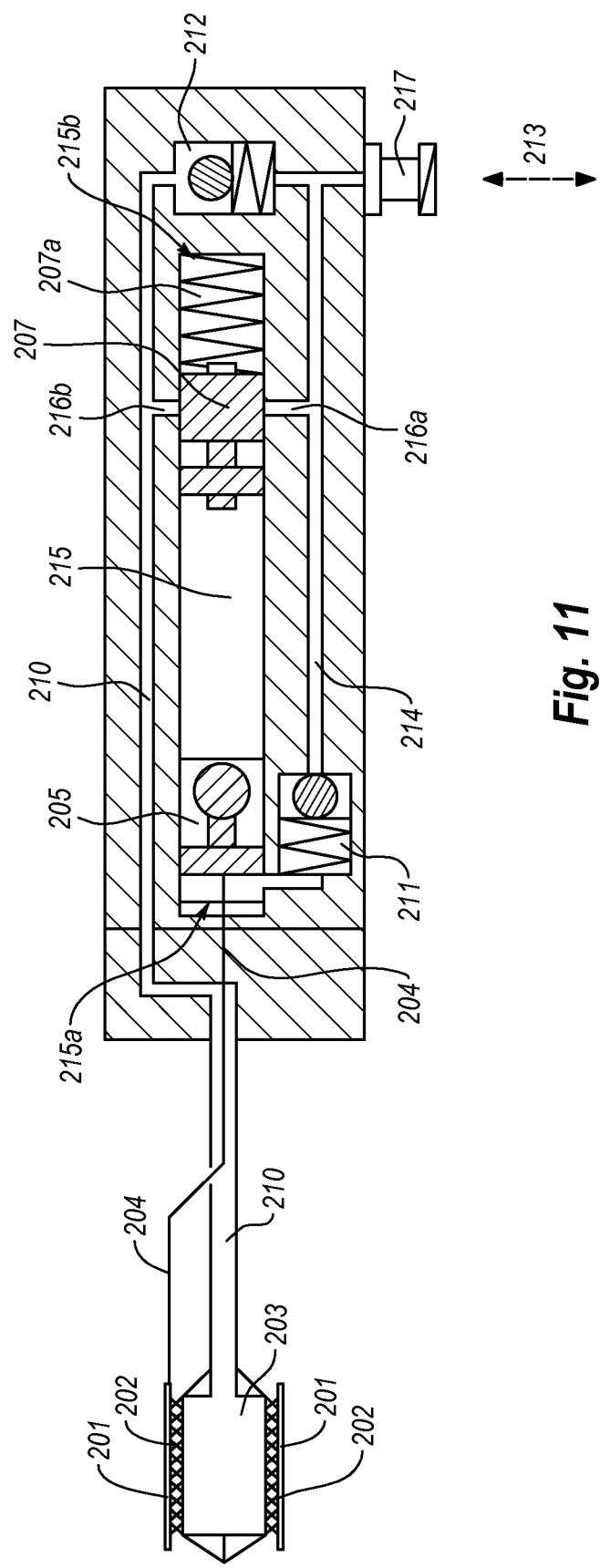
FIG. 11 is a schematic illustration of a third inventive embodiment.
Figure 14:
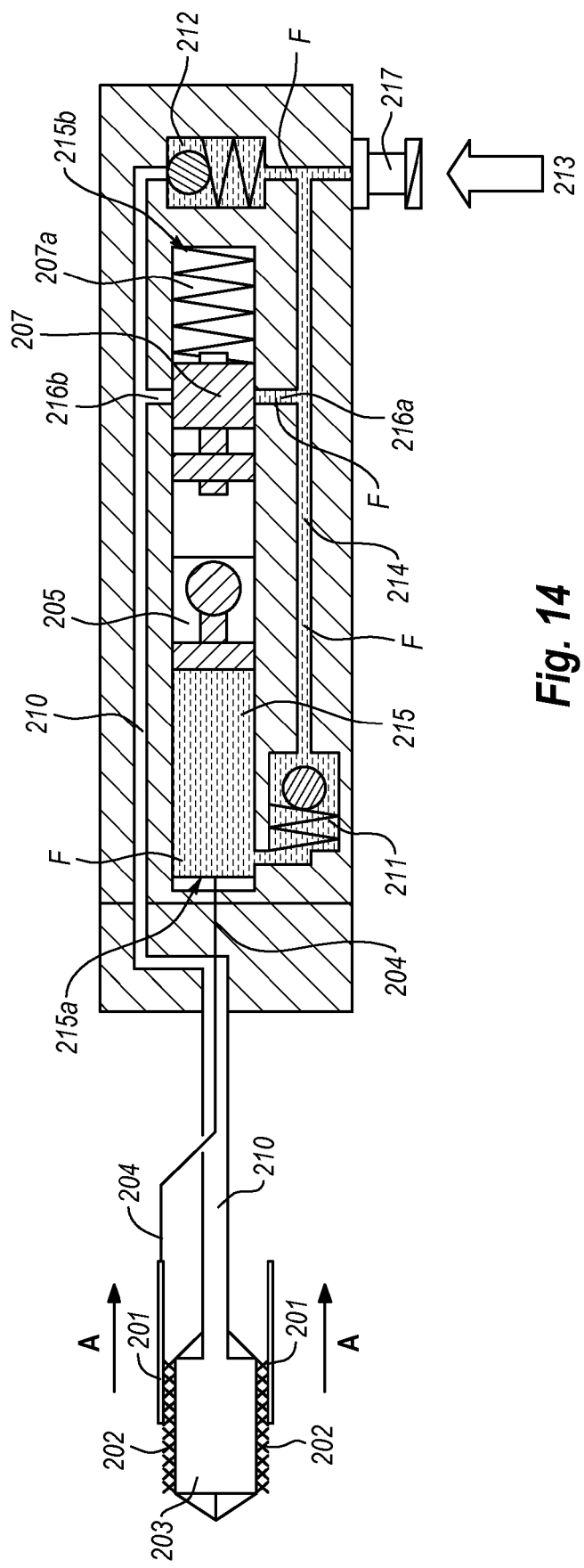
Figure 15:
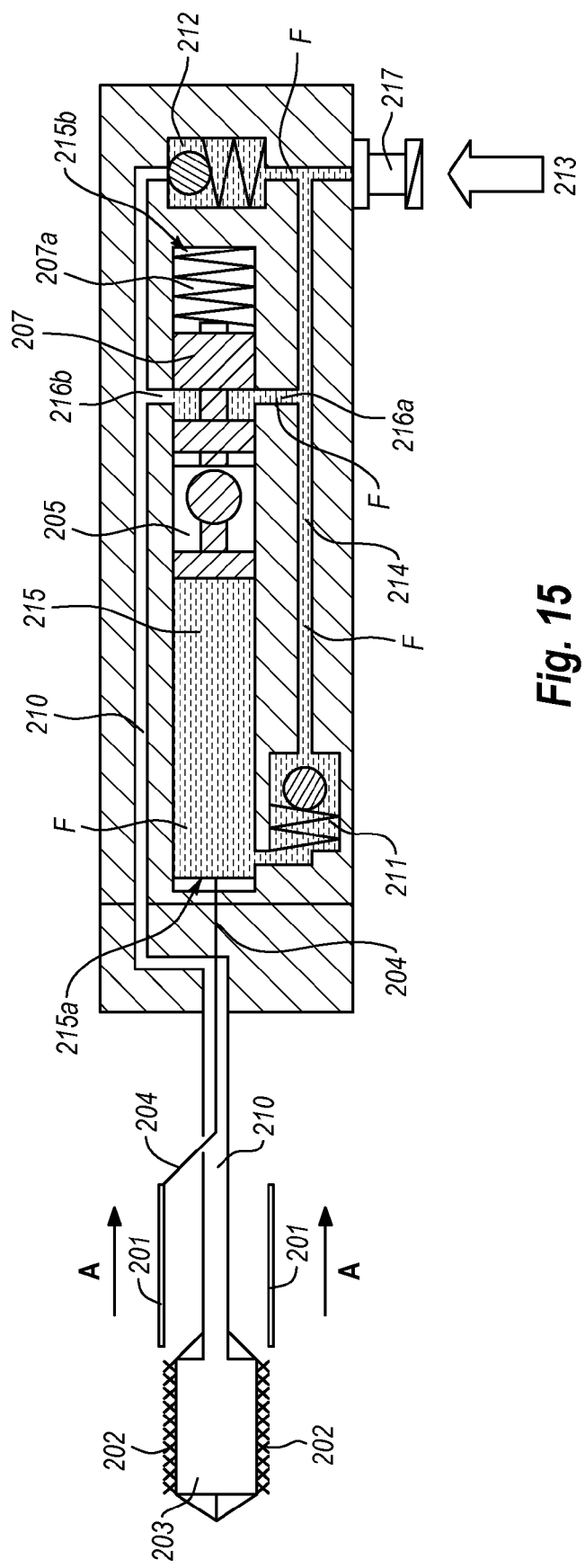
Figure 16:
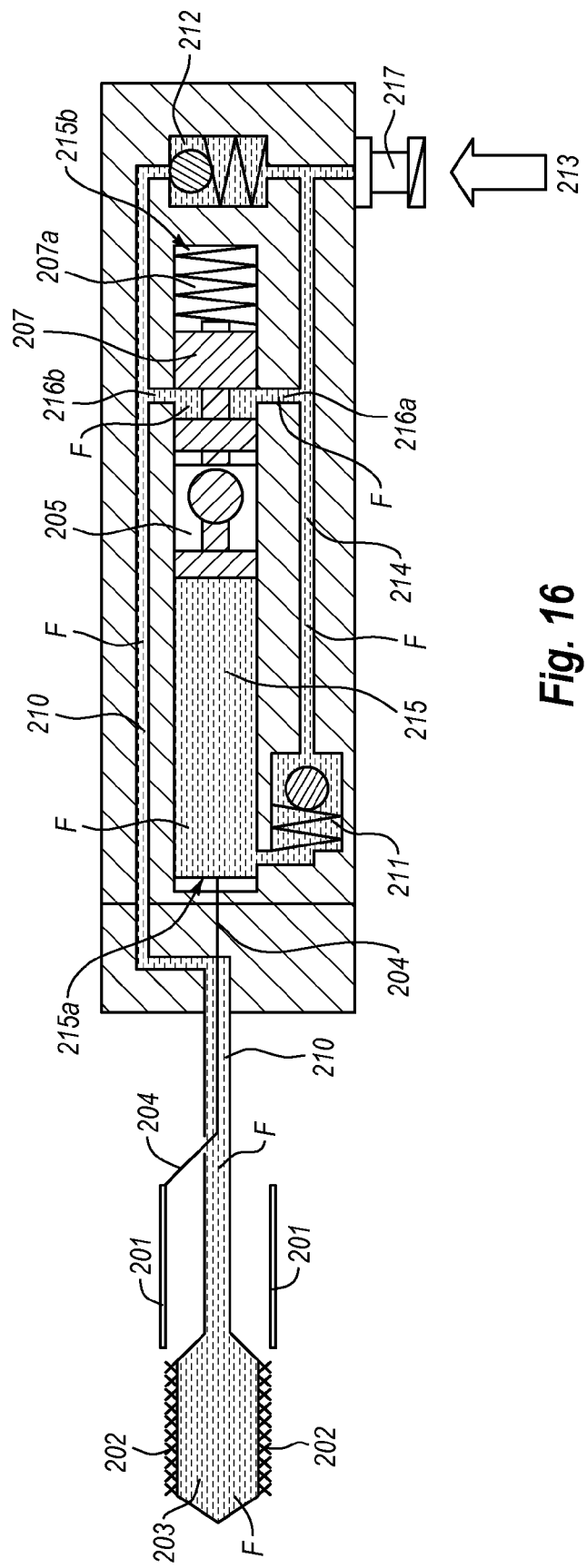
Figure 17:
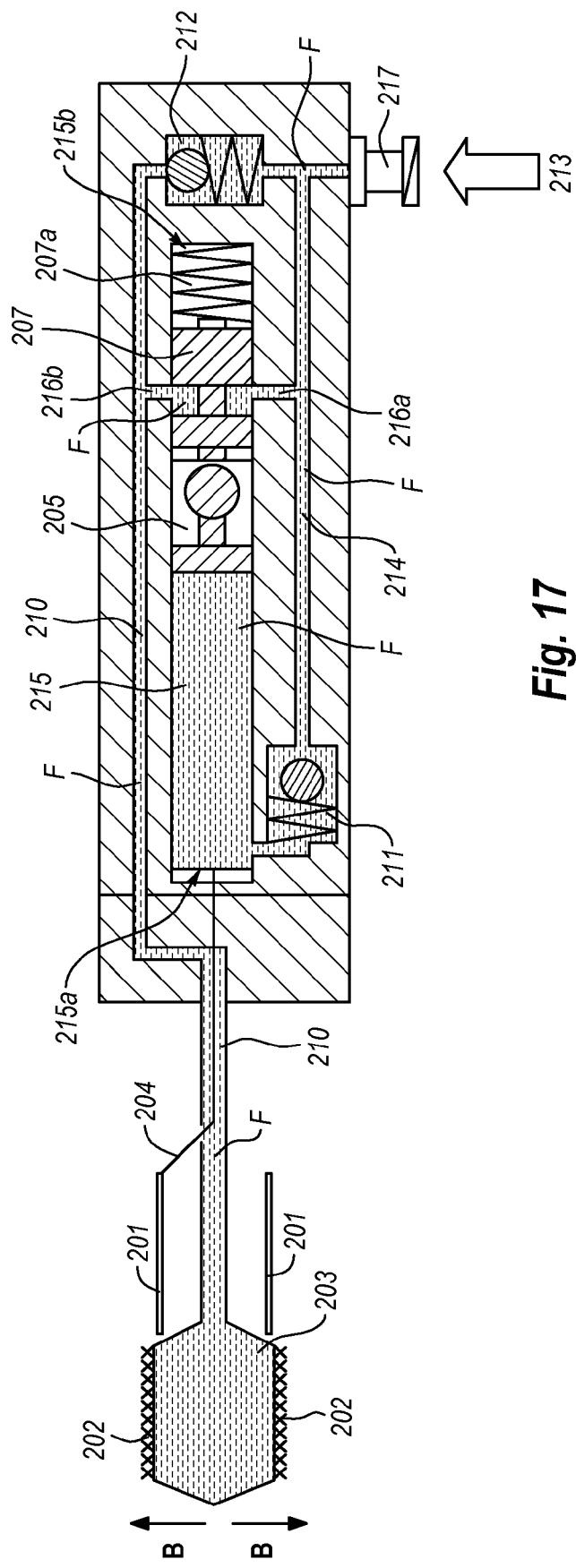

FIG. 11 shows a third inventive embodiment, which differs from the first and second embodiment in the structure of the cylinder-piston arrangement. A two-position valve 207 is located in the cylinder 215; the valve 207 abuts via a spring 207a at the proximal end 215b (right hand side in FIG. 11) of the cylinder 215. In the position shown in FIGS. 11 to 14, the valve 207 shuts two channels 216a, 216b which penetrate the wall of the cylinder 215; channel 216a connects a fluid pressure line 214 from the fluid pressure device 213 with a fluid pressure line 210 which applies the fluid pressure to the expandable means (balloon) 203. When the piston 205 starting from the space 215a at the distal end of the cylinder 215 arrives at the two-position valve 207, it pushes the valve (to the right in FIG. 15) and opens the channels 216a and 216b. Thus, pressurized fluid F from the inflation/deflation device 213 enters the balloon 203 via the line 214, the channels 216a and 216b and the line 210 (FIGS. 15 to 17).

The steps of the method of operation of the third inventive embodiment are shown with respect to FIGS. 12-19.

Figure 12:
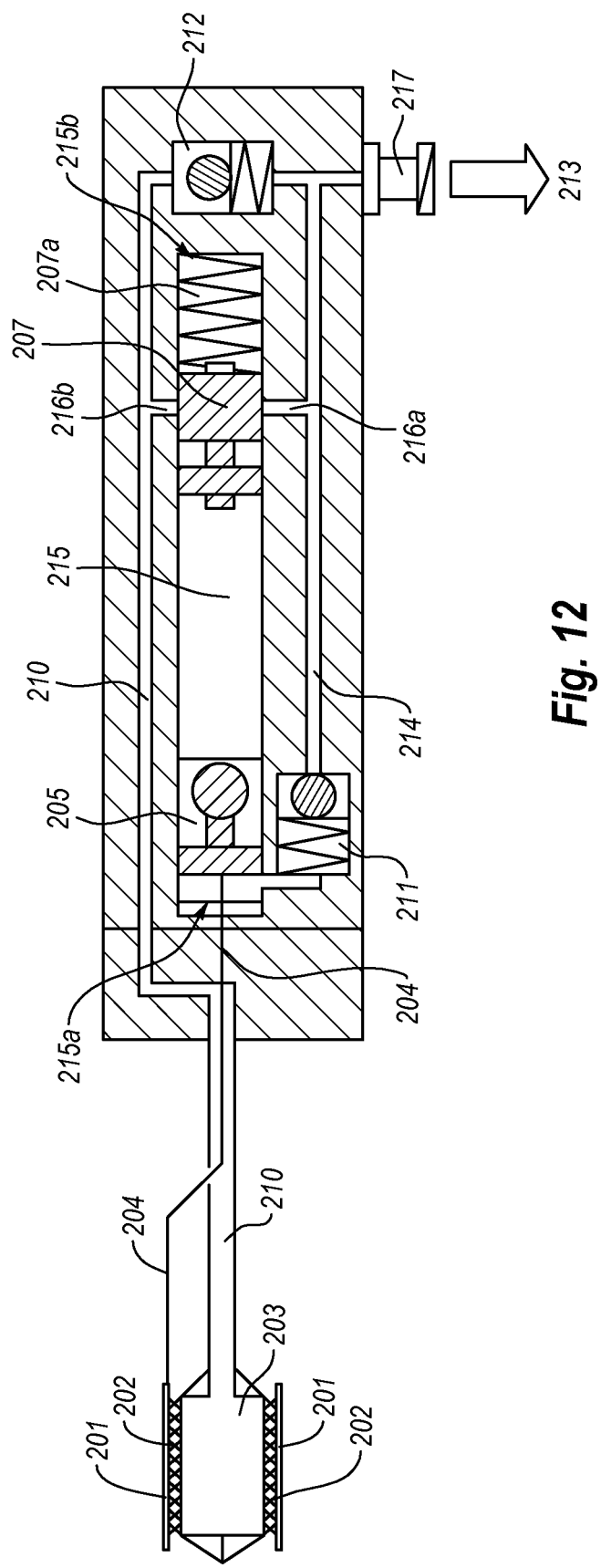
FIGS. 12-19 show steps of the method of operation of the third inventive embodiment.
Figure 13:
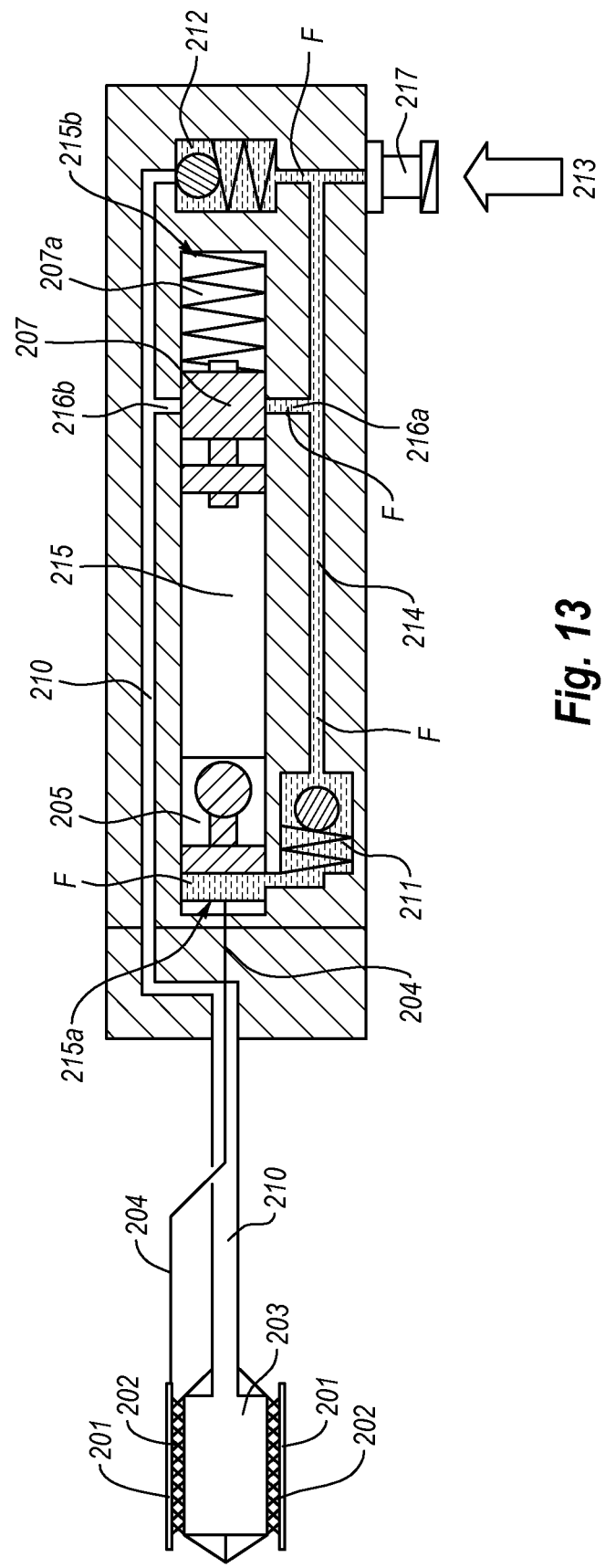
Figure 18:
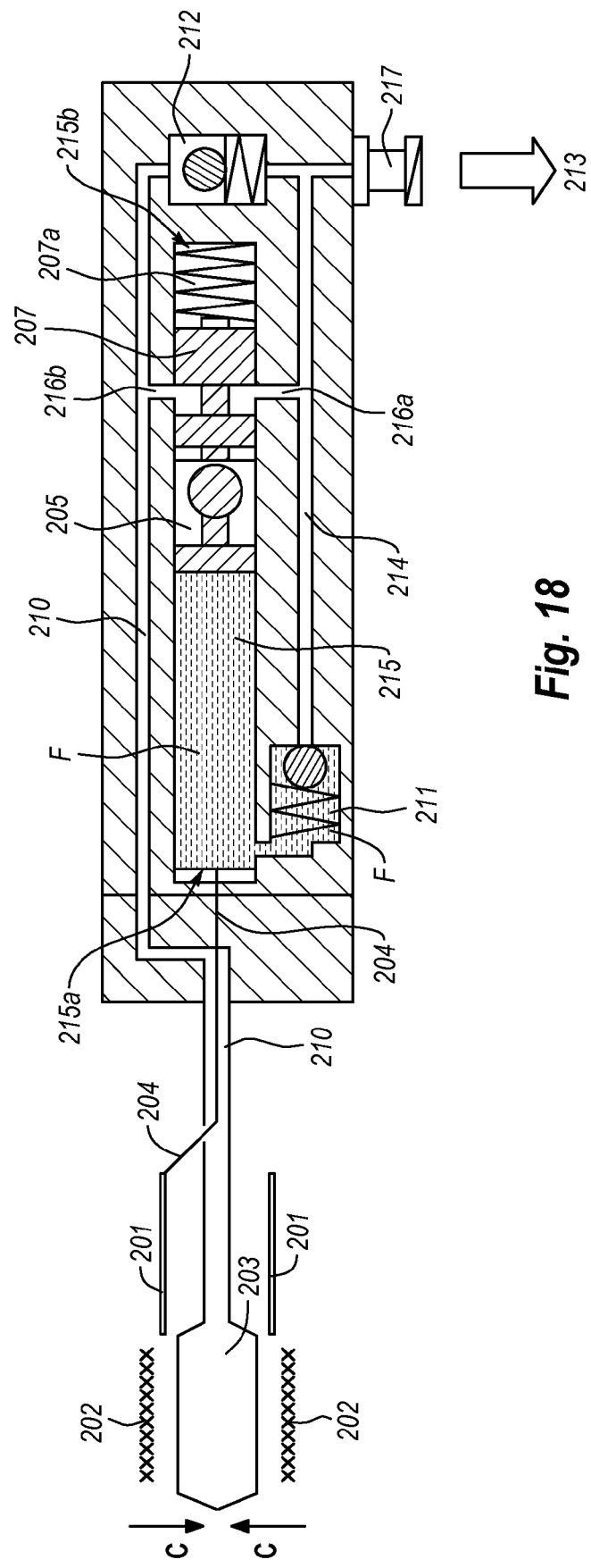
Figure 19:
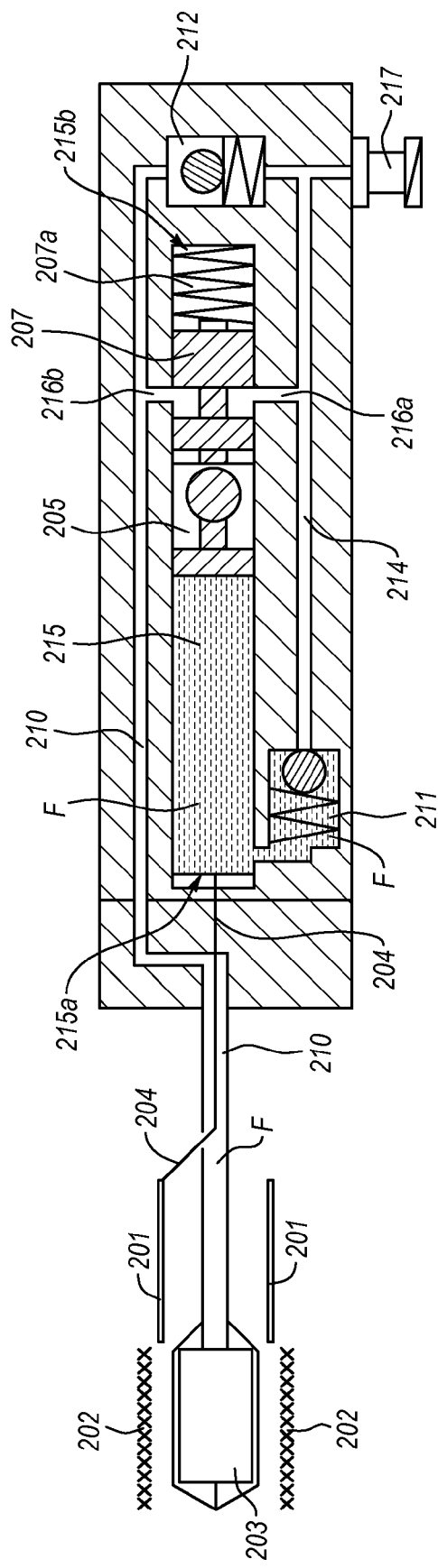

Before operating, a vacuum is applied in order to purge air from the catheter and the sheath retraction apparatus by means of the inflation/deflation device 213. Thereby, the unidirectional valve 212 is opened and the unidirectional valve 211 is closed so that space 215a at the distal end of the cylinder 215 at the left-hand side of the piston 205 remains open (FIG. 12). In FIG. 13, pressurized fluid F from the inflation/deflation device 213 enters the space 215a of the cylinder 215 behind the piston 205 via the line 214 and the unidirectional valve 211, while the unidirectional valve 212 and the channels 216a and 216b are closed. Thereafter, the piston 205 moves in proximal direction (to the right in FIG. 14) and withdraws the protective cover sheath 201 from the stent 202 in the direction of arrows A (FIG. 14). After the protective cover sheath 201 is fully retracted, the piston 205 pushes the valve 207 against the force of the spring 207a into an open position, and the connection between the line 214 and the line 210 via the channels 216a and 216b is opened (FIG. 15). As shown in FIG. 16, pressurized fluid F flows via the line 214, the channels 216a and 216b and the line 210 to the balloon 203. While the unidirectional valve 211 remains open and pressurized fluid F acts against the piston 205 and pushes it to the right in FIG. 17, the two-position valve 207 remains in its open position. The balloon 203 expands in the direction of arrows B and the stent is deployed (FIG. 17) and contacts the wall of the blood vessel (not shown). Thereafter, vacuum is again applied from the inflation/deflation device 213 and the balloon 203 deflates in the direction of arrows C (FIG. 18). The unidirectional valve 211 is closed and the pressurized fluid behind the piston 205 acts on the piston 205 such that the piston 205 and the sheath 201 remain fixed (FIG. 18). In the final state shown in FIG. 19, the catheter is fully purged and the balloon can be re-inflated if necessary. The pressurized fluid F holds the two-position valve 207 open and locks the sheath 201 in the retracted position. If the retraction apparatus will be used one time only, it can be removed. If the retraction apparatus will be re-used, the fluid F is purged from the cylinder 215 by opening the unidirectional valve 211 and pulling the piston 205 to the distal end 215a.

The fluid pressure for operating the refraction device and the expandable means can be controlled in such a manner that the retraction device and the expandable means work concurrently or sequentially, e.g. in order to control the correct position of the stent.

It is an essential feature of the invention that the refraction of the sheath 1, 101 and 201, respectively, namely at the end of the retraction step, automatically controls the deployment (expansion) of the stent 2, 102 and 202, respectively. An operator can easily deploy a stent with a protection sheath simply by activating the inflation/deflation device.

The invention claimed is:

1. An apparatus for delivery and deployment of a medical device within a patient, the apparatus comprising:
a catheter having a proximal end and a distal end;
a deployable medical device arranged at the distal end of the catheter having a delivery configuration and a deployed configuration; and
a sheath being slidably mounted over the medical device and being arranged for proximal retraction from over the medical device by a retraction device, the retraction device comprises a cylinder-piston arrangement operated by a pressurized fluid of a liquid in the catheter;
wherein the cylinder-piston arrangement further comprises a first valve and a second valve, the first valve opens to allow the pressurized fluid to retract the sheath and, after the sheath is retracted, the second valve then opens to allow the pressurized fluid to deploy the medical device from the delivery configuration to the deployed configuration.

2. The apparatus according to claim 1, further comprising source of the pressurized fluid for controlling fluid pressure operating the retraction device.

3. The apparatus according to claim 2, wherein the medical device is mounted at the distal end of the catheter and is responsive to the source of the pressurized fluid to deploy the medical device from the delivery configuration to the deployed configuration.

4. The apparatus according to claim 1, wherein a first piston of the cylinder-piston arrangement is connected to the sheath via a wire.

5. An apparatus for delivery and deployment of a medical device within a patient, the apparatus comprising:
a catheter having a proximal end and a distal end;
a deployable medical device arranged at the distal end of the catheter having a delivery configuration and a deployed configuration; and
a sheath being slidably mounted over the medical device and being arranged for proximal retraction from over the medical device by a retraction device wherein the retraction device comprises a cylinder-piston arrangement operated by a pressurized fluid in the catheter;
wherein the cylinder-piston arrangement further comprises a first valve and a second valve, the first valve opens to allow the pressurized fluid to retract the sheath and, after the sheath is retracted, the second valve then opens to allow the pressurized fluid to deploy the medical device from the delivery configuration to the deployed configuration.

6. The apparatus according to claim 5, wherein the cylinder-piston arrangement comprises a cylinder having a proximal end, a distal end and an outlet located proximate the proximal end, and the cylinder-piston arrangement further comprises a first piston and a floating second piston for controlling opening/closing of the outlet.

7. The apparatus according to claim 6, wherein during retraction of the sheath either the first piston or the second piston closes the outlet, and after at least partial retraction of the sheath the first and second pistons are in a position at the proximal end of the cylinder and the outlet is open.

8. The apparatus according to claim 7, wherein the first piston comprises a hook, the second piston comprises a first central opening, the cylinder comprises a second opening and a hook holder at its proximal end, so that during retraction of the sheath the first piston moves the hook through the first opening and the second opening until the hook engages the hook holder.

9. The apparatus according to claim 6 wherein a first piston arrangement comprises a first connector and the cylinder comprises at its proximal end a second connector having a configuration that is complementary to the first connector, so that after retraction of the sheath the first connector engages the second connector and the outlet is in connection with the fluid pressure acting on the first piston.

10. The apparatus according to claim 5, wherein the medical device is mounted at the distal end of the catheter and is responsive to a fluid pressure device to deploy the medical device from the delivery configuration to the deployed configuration.

11. The apparatus according to claim 5, wherein the cylinder-piston arrangement is further arranged for operating the retraction device so that the medical device is deployed from its delivery configuration to its deployed configuration in response to the retraction of the sheath and wherein the cylinder-piston arrangement comprises an outlet connected to a fluid pressure line for applying the pressurized fluid to deploy the medical device.

12. A system for delivery and deployment of a medical device within a patient, the system comprising:
a catheter having a proximal end and a distal end;
a medical device arranged at the distal end of the catheter having a delivery configuration and a deployed configuration;
a sheath being slidably mounted about the catheter and being arranged for proximal retraction to expose the medical device by a retraction device, the retraction device comprising a cylinder-piston arrangement operated by a pressurized fluid from a fluid pressure device, the fluid pressure device is arranged for operating the retraction device; and
wherein the cylinder-piston arrangement further comprises a first valve and a second valve, the first valve opens to allow the pressurized fluid to retract the sheath and, after the sheath is retracted, the second valve then opens to allow the pressurized fluid to deploy the medical device from the delivery configuration to the deployed configuration.

13. The system according to claim 12, wherein the cylinder-piston arrangement comprises a cylinder having a proximal end, a distal end and an outlet located proximate the proximal end, and the cylinder-piston arrangement further comprises a first piston and a floating second piston for controlling opening/closing of the outlet.

14. The system according to claim 13, wherein during retraction of the sheath either the first piston or the second piston closes the outlet, and after at least partial retraction of the sheath the first and second pistons are in a position at the proximal end of the cylinder and the outlet is open.

15. The system according to claim 14, wherein the first piston comprises a hook, the second piston comprises a first central opening, the cylinder comprises a second opening and a hook holder at its proximal end, so that during retraction of the sheath the first piston moves the hook through the first opening and the second opening until the hook engages the hook holder.

16. The according to claim 13 wherein a first piston arrangement comprises a first connector and the cylinder comprises at its proximal end a second connector-having a configuration that is complementary to the first connector, so that after retraction of the sheath the first connector engages the second connector and the outlet is in connection with the fluid pressure acting on the first piston.

17. A method for delivery and deployment of a medical device within a patient, the method comprising:
   positioning a medical device within a patient using an apparatus for delivery and deployment of a medical device within a patient, the apparatus including:
   a catheter having a proximal end and a distal end;
   a deployable medical device arranged at the distal end of the catheter having a delivery configuration and a deployed configuration; and
   a sheath being slidably mounted over the medical device and being arranged for proximal retraction from over the medical device by a retraction device, the retraction device comprises a cylinder-piston arrangement operated by a pressurized fluid of a liquid in the catheter;
   wherein the cylinder-piston arrangement further comprises a first valve and a second valve, the first valve opens to allow the pressurized fluid to retract the sheath and, after the sheath is retracted, the second valve then opens to allow the pressurized fluid to deploy the medical device from the delivery configuration to the deployed configuration; pressurizing a liquid within the catheter; and automatically proximally retracting the sheath to expose the medical device.

18. The method of claim 17, wherein automatically proximally retracting the sheath to expose the medical device further comprises activating the cylinder-piston arrangement operated by the fluid pressure of the liquid.

* * * * *